United States Patent [19]

Uldall

[11] Patent Number: 4,821,718
[45] Date of Patent: Apr. 18, 1989

[54] SURGICAL INSTRUMENT FOR PROSTHETIC GRAFT REMOVAL

[76] Inventor: P. Robert Uldall, 11 Birchwood Avenue, Willowdale, Ontario, Canada, M2L 1M2

[21] Appl. No.: 109,516

[22] Filed: Oct. 19, 1987

[51] Int. Cl.4 .............................................. A61B 17/32
[52] U.S. Cl. .................................................. 128/305
[58] Field of Search .................. 128/305, 303 R, 753, 128/754

[56] References Cited

U.S. PATENT DOCUMENTS

| | | |
|---|---|---|
| 2,473,968 | 6/1949 | Paton . |
| 2,779,334 | 1/1957 | Sandborn . |
| 2,788,787 | 4/1957 | Trace . |
| 2,868,206 | 1/1959 | Stoesser . |
| 3,788,325 | 1/1974 | Jacobsen . |
| 3,855,996 | 12/1974 | Bolduc . |

FOREIGN PATENT DOCUMENTS

| | | | |
|---|---|---|---|
| 3525917 | 2/1986 | Fed. Rep. of Germany | 128/305 |
| 380319 | 9/1973 | U.S.S.R. | 128/305 |
| 651802 | 3/1979 | U.S.S.R. | 128/305 |
| 1204199 | 1/1986 | U.S.S.R. | 128/305 |

OTHER PUBLICATIONS

Martin Motor Trephine Pamphlet (5-1977).

Primary Examiner—Michael H. Thaler
Attorney, Agent, or Firm—Ridout & Maybee

[57] ABSTRACT

A surgical instrument is provided for removal of prosthetic vein grafts from surrounding tissues. The instrument comprises a cylindrical knife having a sharp circular front edge, a concentric annular guide and an elongate arm with an offset handle at its end. The graft is drawn through the interior of the instrument, and the configuration of the exterior of the instrument is such that the surrounding tissue is retracted from the graft, so that the tissue peels from the graft at the point at which the sharp circular front edge of the cylindrical knife is brought to bear.

12 Claims, 2 Drawing Sheets

SURGICAL INSTRUMENT FOR PROSTHETIC GRAFT REMOVAL

BRIEF SUMMARY OF THE INVENTION

A surgical instrument is provided for removal of prosthetic grafts from surrounding tissue. The instrument comprises a cylindrical knife having a sharp circular front edge, a concentric annular guide and an elongate arm with a handle at its end, preferably offset from the axis of the knife, guide and arm. The graft is drawn through the interior of the cylindrical knife and annular guide, and the instrument passed over the graft between two incisions tunnelling under the overlying tissue by applying forwardly compressive and rotating forces to the handle. The annular guide retracts the prosthetic graft and the surrounding tissue away from one another so that these are tending to peel apart at the point at which the sharp edge of the knife is applied.

DETAILED DESCRIPTION

A surgical instrument is provided for removal of prosthetic grafts from the surrounding tissue.

Figure 2:
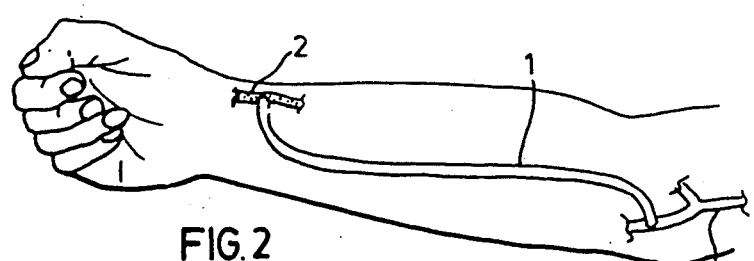
FIG. 2 is a view of a straight graft implanted under the skin tissue layer of the right forearm.
Figure 3:
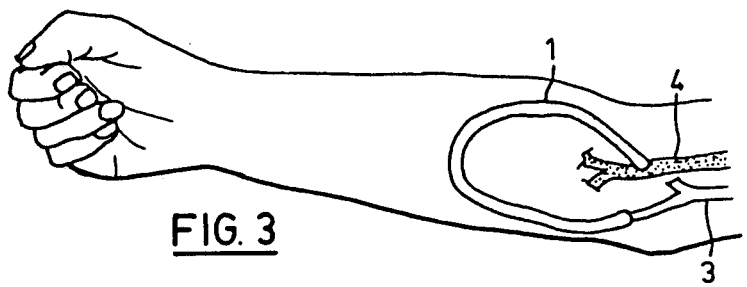
FIG. 3 is a view of a loop graft implanted under the skin tissue layer of the right forearm.

In order to facilitate hemodialysis for patients with difficulties of vascular access, a prosthetic tubular graft for example of polytetrafluorethylene or bovine origin is as shown in FIGS. 2 and 3 implanted in a patient's forearm, wherein one end of the graft 1 is anastomosed end to side on to an artery, while the other end is anastomosed end to side on to a vein. Two types of common grafts are a straight graft shown in FIG. 2 from the radial artery 2 to the antecubital vein 3, and a loop graft shown in FIG. 3 from the brachial artery 4 to the antecubital vein 3. The graft may sometimes become infected or may erode through the skin thereby requiring removal. Thrombosis may also occur in the graft which, although not detrimental to the patient's health, if left in situ is unsightly.

To remove the graft the patient is anesthetized, and incisions are made transversely across both ends of the graft. The exposed graft is ligated and divided. Depending on the length of the graft a number of incisions are made transversely across the graft at intervals to provide access for removal.

Using conventional surgical instruments and techniques, a surgeon must dissect the graft away from the surrounding tissue in a long and difficult operation which causes significant discomfort and some trauma to the patient.

Figure 1:
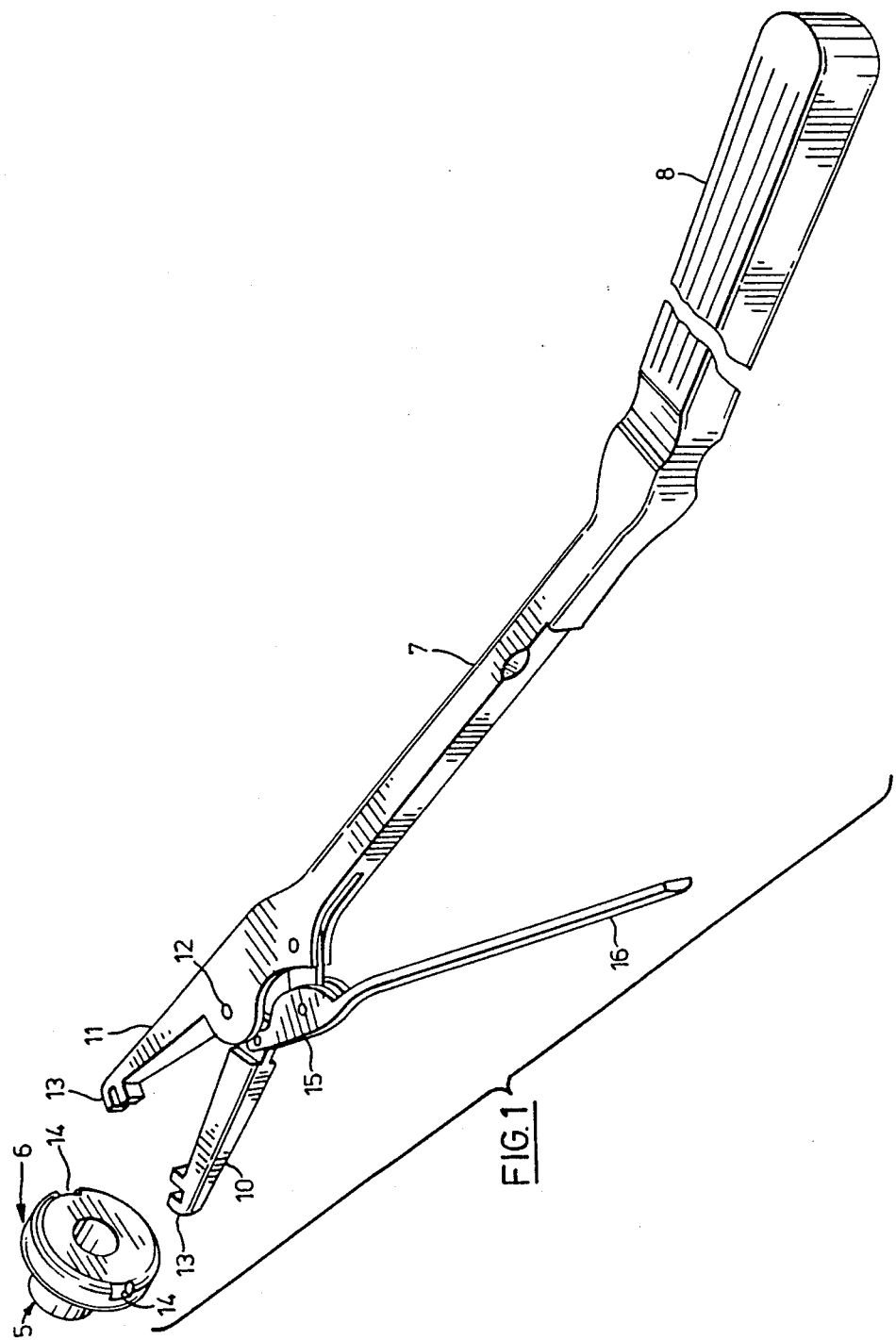
FIG. 1 is a perspective view of the instrument wherein the annular guide is separated from the arm and scissor clamp mechanism.

The present invention shown in FIG. 1 provides a surgical instrument for removal of the prosthetic graft comprising a cylindrical knife 5, an annular guide 6, and an arm 7 with a handle 8 provided on the rear portion thereof.

The cylindrical knife 5 comprised of metal has a sharp circular front edge and a rear portion connected in and secured to a concentric annular guide 6 of resin material.

Figure 4:
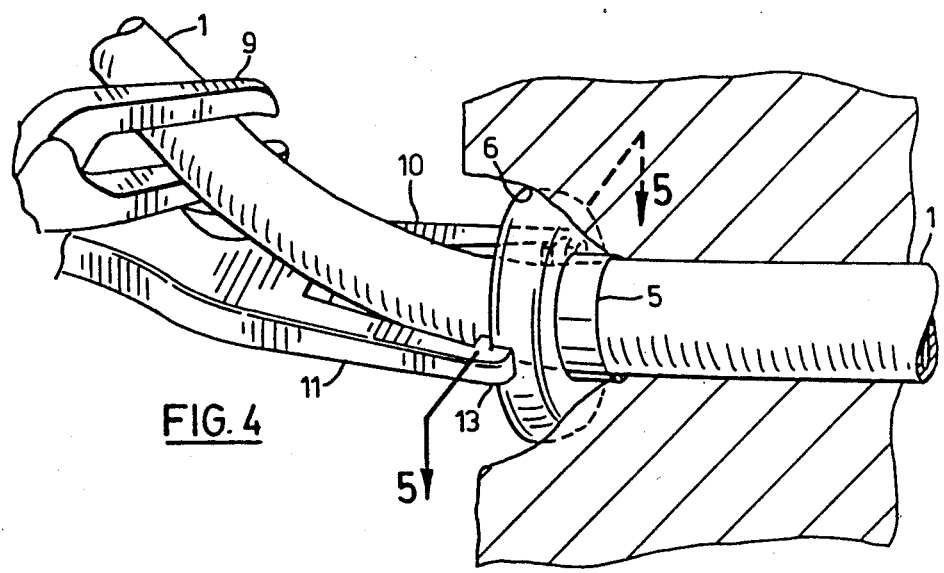
FIG. 4 is a side view partially in section of the surgical instrument in use, showing the prosthetic graft, surrounding tissue and forceps.

To remove the graft 1, as in the conventional method, transverse incisions are made and the exposed graft is ligated and divided. One free end of the graft 1 is drawn by means of a separate instrument through the interior of the cylindrical knife 5, through the central opening of the annular guide 6, and through an aperture 7a in the forward portion of the arm 7. Said free end of the graft 1 is secured by forceps 9 as shown in FIG. 4. The instrument is passed over the graft 1 between successive incisions burrowing under the overlying tissue layer by applying forward and rotating forces to the handle 8, and tensile force to the free end of the graft 1.

The annular guide 6 has an exterior diameter greater than the diameter of the sharp circular front edge of the cylindrical knife 1. The front surface of the guide 6 extends continuously rearwardly from the external surface of the cylindrical knife 5, and merges arcuately smoothly with the cylindrical side surface of the annular guide 6. The rear surface of the guide 6 also merges arcuately smoothly with the cylindrical side surface of the guide 6. These exterior features of the instrument retract the surrounding tissue internally outwardly away from the prosthetic graft 1 as the instrument is passed forwardly over the graft 1, and enable the tissue to slide freely over the exterior of the instrument.

The central opening in the annular guide 6 communicates with the interior of the cylindrical knife 5 and the aperture 7a in the forward portion of the arm 7, whereby the freed portion of the prosthetic graft 1 to be removed is passed through the instrument. Preferably, the sharp circular front edge of the cylindrical knife 5 is formed by a beveled surface 5a on the internal surface of the cylindrical knife 5 whereby the graft 1 passes through the knife intact, without tending to be severed on an interior sharp edge. Merely by way of example, it may be mentioned that the internal diameter of the knife 5 may be about 7 mm. The diameter of the central opening in the annular guide 6 is preferably less than the internal diameter of the cylindrical knife 5 and the internal surface of the opening extends smoothly continuously rearwardly from the internal surface of the cylindrical knife 5. Advantageously, the internal surface of the central opening in the annular guide 6 merges arcuately smoothly with the rear surface of the annular guide 6. These features of the interior of the instrument assist in retracting the prosthetic graft 1 inwardly away from the surrounding tissue as the instrument is passed forwardly over the graft 1, and enable the freed portion of the prosthetic graft 1 to slide freely through the interior of the instrument.

The combined effect of the exterior of the instrument retracting the surrounding tissue away from the prosthetic graft 1, and the interior of the instrument together with tensile forces applied to the free end of the graft retracting the prosthetic graft 1 away from the surrounding tissue, presents the cylindrical knife 5 with a circle or tunnel of parting, so that at the zone at which the tip or sharp edge of the blade engages, the graft and tissue are at the point of peeling away from one another. The separating is assisted by applying forward and rotating forces to the handle of the instrument.

The extent to which the tissue is retracted from the graft before being engaged by the cylindrical knife 5 is determined by the angle at which the surrounding tissue is separated or deflected from the graft 1 by the exterior of the guide 6 as tissue slides over the exterior of the instrument. Preferably, the most forward circular line of maximum diameter of the annular guide 6 is positioned relative to the sharp circular front edge of the knife 1 such that the angle between the axis of the instrument and a frustoconical surface drawn between the sharp circular front edge and the most forward circular line of maximum diameter of the annular guide 6 is in the range from 35° to 55°, more preferably about 40° to 50°.

The free portion of the prosthetic graft 1 is passed through aperture 7a in the forward portion of the arm 7. To the rear of the annular guide 6 the arm 7 and the free portion of the prosthetic graft 1 occupy the longitudinal cavity between the layers of tissue through which the forward portion of the instrument has been passed. When the cylindrical knife 5 and annular guide 6 of the instrument have been passed from an incision to the next successive incision, the instrument is withdrawn backwards and removed through the previous incision. The free portion of the graft 1 is divided at the succeeding incision and removed. The operation procedure is repeated through successive incisions until the entire graft 1 is removed.

Desirably, the arm 7 is of such length that the instrument can be extended under the skin for a length of about one half the length of a typical graft, so that the entire graft may be removed making one incision at each end of the graft and one in the middle. The arm 7 is of cross-section considerably smaller than guide 6 so that the skin rearwardly along the tunnel from which the graft has been separated is not stretched.

The handle 8 desirably extends at an angle from the axis along which the knife 5, guide 6 and arm 7 are disposed to provide a gripping portion offset from said axis. This facilitates gripping the instrument and applying rotating forces to the knife 5 while tunnelling the knife 5 under the skin along the graft.

Preferably, the handle 8 and arm 7 of the instrument are separable from the cutting head comprising the annular guide 6 and cylindrical knife 5. The annular guide 6, made of smoothly molded resin material and the metallic cylindrical knife 5 embedded therein are disposable after a single use, whereas the handle 8 and arm 7 are repeatedly used after sterilization as with conventional surgical instruments.

Figure 5:
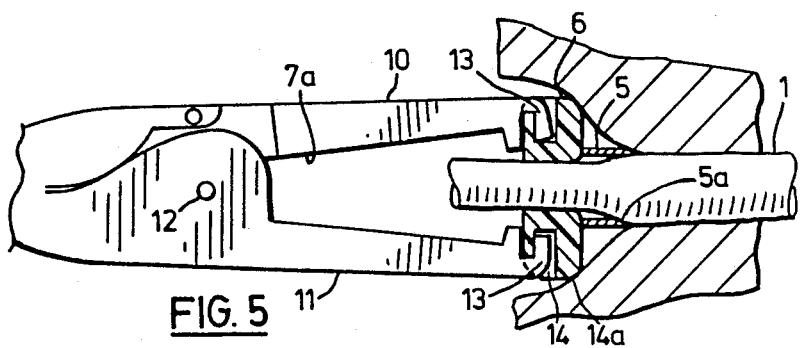
FIG. 5 is a cross-sectional view along lines 5—5 of FIG. 4.

The resin material of the guide 6 should be strong and robust and gas autoclavable so that the replacement blades and guide units may be provided as sterile packages. The annular guide 6 is connected to the arm 7 by a clamping mechanism comprised of two fingers 10 and 11 shown in FIGS. 1, 4 and 5 at the forward end of the arm 7, finger 10 pivoting relative to finger 11 about a pin 12 at the pivot axis. The two fingers 10 and 11 have at their forward ends projections 13 which engage diametrically opposing recesses 14 in a cylindrical side surface 14a of the annular guide 6. As seen in FIG. 5, the recesses 14 extend radially inwardly from side surface 14a, so that the projections 13 may be inserted radially thereinto on closure of fingers 10 and 11. In the preferred embodiment, the fingers 10 and 11 are locked in a closed position gripping the annular ring 6 by means of a toggle clamp mechanism 15 at the forward end of the arm, engaged by rotating lever 16 toward arm 7.

I claim:

1. An instrument for removal of a prosthetic graft from surrounding tissue comprising a cylindrical knife having a sharp circular front edge, a rear portion of said knife being connected in and secured to an annular guide concentric with said cylindrical knife and of external diameter greater than the diameter of said sharp circular front edge, the front surface of said guide extending continuously rearwardly from the external surface of said knife and merging arcuately smoothly with the side surface of the guide, whereby tissue may slide freely over said front surface, an arm connected to said guide having an aperture communicating with the central opening in said annular guide, through which the freed portion of the prosthetic graft can be withdrawn rearwardly, and a handle provided on the rear portion of said arm the diameter of the opening in the annular guide being less than the internal diameter of the cylindrical knife, the internal surface of said central opening extending smoothly continuously rearwardly from the internal surface of said cylindrical knife whereby the freed portion of the prosthetic graft may slide freely over said internal surface.

2. The instrument of claim 1 wherein the sharp circular front edge of the cylindrical knife is formed by a beveled surface on the internal surface thereof.

3. The instrument of claim 1 wherein the angle between the external surface of the cylindrical knife, and a frustoconical surface drawn from the sharp circular front edges of said cylindrical knife to the most forward circular line of maximum diameter of the annular guide is in the range from 35° to 55°.

4. The instrument of claim 3 wherein said angle is in the range from 40° to 50°.

5. The instrument of claim 1 wherein the front and rear surfaces of the annular guide merge arcuately smoothly with the exterior side surface of the annular guide and the inner surface of the central opening whereby tissue may slide freely over said rear surface and exterior side surface of the annular guide and the freed portion of the prosthetic graft may slide freely over said rear surface and inner surface of said central openings of the annular guide.

6. The instrument of claim 1 wherein the annular guide comprises resin material.

7. The instrument of claim 1 wherein the cylindrical knife comprises of metal with the rear portion of said knife embedded in an annular guide of resin material.

8. The instrument of claim 1 wherein the maximum cross-sectional dimension of the arm is less than the external diameter of the annular guide.

9. The instrument of claim 1 wherein the handle provides a gripping portion which is offset laterally from an axis along which the knife, guide and arm extend.

10. A cutting head for an instrument for removal of a prosthetic graft from surrounding tissue, said cutting head comprising a cylindrical knife having a sharp circular front edge, a rear portion of said knife being connected in and secured to an annular guide concentric with said cylindrical knife and of external diameter greater than the diameter of said sharp circular front edge, the front surface of said guide extending continuously rearwardly from the external surface of said knife and merging arcuately smoothly with the side surface of the knife, whereby tissue may slide freely over said front surface and the freed end of the prosthetic graft can be withdrawn rearwardly through the central opening in said annular guide and knife, the diameter of the opening in the annular guide being less than the internal diameter of the cylindrical knife, the internal surface of the opening extending smoothly continuously rearwardly from the internal portion of the knife, whereby the freed portion of the prosthetic graft may slide freely over said internal surface, and said guide comprising a cylindrical side surface having therein a pair of diametrically opposed recesses, each recess extending radially inwardly from said side surface, for receiving and engaging a projection on said instrument to be inserted radially inwards into each recess.

11. A cutting head in accordance with claim 10 wherein the sharp circular front edge of the cylindrical knife is formed by a beveled surface on the interior surface of said cylindrical knife.

12. An instrument for removal of a prosthetic graft from surrounding tissue comprising a cylindrical knife having a sharp circular front edge, a rear portion of said knife being connected in and secured to an annular guide concentric with said cylindrical knife and of external diameter greater than the diameter of said sharp circular front edge, the front surface of said guide extending continuously rearwardly from the external surface of said knife and merging arcuately smoothly with the side surface of the guide, whereby tissue may slide freely over said front surface, an arm separably connected to said guide by a clamp mechanism comprising two fingers at the forward end of the arm pivoting relative to one another by the pivot axis, each finger having a projection on its distal end engaging a recess in the rear surface of the annular guide, and means to lock said fingers in said recesses in a closed position, the arm having an aperture communicating with the central opening in said annular guide, through which the freed portion of the prosthetic graft can be withdrawn rearwardly and a handle provided on the rear portion of said arm.

* * * * *